US009872959B2

(12) United States Patent
Yodfat et al.

(10) Patent No.: US 9,872,959 B2
(45) **Date of Patent: *Jan. 23, 2018**

(54) METHOD SYSTEM AND DEVICE FOR ASSESSING INSULIN SENSITIVITY

(71) Applicant: Roche Diabetes Care, Inc., Indianapolis, IN (US)

(72) Inventors: Ofer Yodfat, Maccabim-Reut (IL); Gali Shapira, Haifa (IL); Iddo Gescheit, Tel-Aviv (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,935

(22) Filed: Dec. 21, 2015

(65) Prior Publication Data

US 2016/0106918 A1 Apr. 21, 2016

Related U.S. Application Data

(63) Continuation of application No. 12/145,942, filed on Jun. 25, 2008, now Pat. No. 9,244,077.

(60) Provisional application No. 60/937,247, filed on Jun. 25, 2007.

(51) Int. Cl.

| | |
|---|---|
| ***A61M 31/00*** | (2006.01) |
| ***G01N 33/66*** | (2006.01) |
| ***G06F 19/00*** | (2011.01) |
| ***G06F 19/22*** | (2011.01) |
| ***A61M 5/142*** | (2006.01) |
| ***A61M 5/172*** | (2006.01) |
| ***A61M 5/14*** | (2006.01) |

(52) U.S. Cl.

CPC ........ *A61M 5/1723* (2013.01); *A61M 5/1413* (2013.01); *A61M 5/14244* (2013.01); *G01N 33/66* (2013.01); *G06F 19/3437* (2013.01); *G06F 19/3456* (2013.01); *A61M 5/14248* (2013.01); *A61M 2005/14296* (2013.01); *A61M 2230/20* (2013.01); *G01N 2800/042* (2013.01)

(58) Field of Classification Search

None

See application file for complete search history.

(56) References Cited

U.S. PATENT DOCUMENTS

| | | | | |
|---|---|---|---|---|
| 5,822,715 | A | 10/1998 | Worthington et al. | |
| 6,936,029 | B2 | 8/2005 | Mann et al. | |
| 9,119,582 | B2 * | 9/2015 | Jennewine ........ | A61M 5/14248 |
| 2004/0248204 | A1 | 12/2004 | Moerman | |
| 2005/0272640 | A1 | 12/2005 | Doyle et al. | |
| 2007/0060871 | A1 | 3/2007 | Istoc et al. | |
| 2007/0191702 | A1 | 8/2007 | Yodfat et al. | |
| 2008/0119707 | A1 | 5/2008 | Stafford | |
| 2008/0125700 | A1 | 5/2008 | Moberg et al. | |
| 2008/0215035 | A1 | 9/2008 | Yodfat et al. | |

FOREIGN PATENT DOCUMENTS

| | | | |
|---|---|---|---|
| WO | 2005113036 | A1 | 12/2005 |

OTHER PUBLICATIONS

Chase (Diabetes Technology and Therapeutics, 2005, vol. 7, pp. 274-282).*

Gross et al (Diabetes Technology & Therapeutics, 2003, vol. 5, pp. 365-369).*

Araujo-Vilar et al., "Minimal model of glucose metabolism: modified equations and its application in the study of insulin sensitivity in obese subjects", Diabetes Res. Clin. Practice, 39:129-141 (1998).

Fabietti et al., "Control oriented model of insulin and glucose dynamics in type 1 diabetics", Med. Biol. Eng. Comput., 44:69-78 (2006).

Fabietti et al., "Clinical validation of a new control-oriented model of insulin and glucose dynamics in subjects with type 1 diabetes", Diabetes Technol. Therap., 9(4):327-338 (2007).

King et al., "Basal bolus dosing: a clinical experience", Cur. Diabetes Rev., 1(2):215-220 (2005).

Wallace et al., "Use and abuse of HOMA modeling", Diabetes Care, 27(6):1487-1495 (2004).

The Diabetes and Complications Trial (DCCT) Research Group, "The Effect of Intensive Treatment of Diabetes on the Development and Progression of Long-Term Complications in Insulin-Dependent Diabetes Mellitus", N. Engl J. Med 329: 977-986 (1993).

UK Prospecive Diabetes Study (UKPDS) Group, Intensive Blood-Glucose Control with Sulphonylureas or Insulin compared with Conventional Treatment and Risk of Complications in Patients with Type 2 Diabetes (UKPDS 33), The Lancet 352: 837-853 (1998).

UK Prospective Diabetes Study (UKPDS) Group, "Tight Blood Pressure Control and Risk of Macrovascular and Microvascular in Type 2 Diabetes: UKPDS 38", BMJ 317, (7160):703-13 (1998).

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", N. Engl J Med 353 (25): 2643-53 (2005).

J. Walsh R. Roberts, C.B. Varma and T. Bailey, "Using Insulin, Everything You Need for Success with Insulin", Torrey Pines Press (2003).

G.M. Steil et al., "Modeling Insulin Action for Development of a Closed-Loop Artificial Pancreas", Diabetes Technology and Therapeutics 7(1) 94-108 (2005).

(Continued)

*Primary Examiner* — Karen Canella

(74) *Attorney, Agent, or Firm* — Dinsmore & Shohl LLP

(57) ABSTRACT

A method and a system for determining insulin sensitivity (IS) is described. In one aspect the method and the system can be implemented by receiving a first parameter corresponding to an insulin dose in a subcutaneous tissue; applying a first kinetic model to obtain a plasma insulin concentration based on the first parameter; receiving a second parameter corresponding to a plasma glucose concentration; determining the insulin sensitivity (IS) based on the plasma insulin concentration and the second parameter.

15 Claims, 7 Drawing Sheets

(56) References Cited

OTHER PUBLICATIONS

Kobayashi et al. "The pharmacokinetics of insulin after continuous subcutaneous infusion or bolus subcutaneous injection in diabetic patients", Diabetes 32, 331-336 (1983).

K. Rebrin et al., "Subcutaneous Glucose Predicts Plasma Glucose Independent of Insulin: Implications for Continuous Monitoring", Am J Physiol Endocinol Metab 277, 561-571 (1999).

* cited by examiner

| TOTAL DAILY INSULIN DOSE (TDD) [IU/DAY] | 2200 RULE [MG/DL] | 2000 RULE [MG/DL] | 1800 RULE [MG/DL] | 1600 RULE [MG/DL] |
|---|---|---|---|---|
| 20 | 110 | 100 | 90 | 80 |
| 25 | 88 | 80 | 72 | 64 |
| 30 | 73 | 67 | 60 | 53 |
| 35 | 63 | 57 | 51 | 46 |
| 40 | 55 | 50 | 45 | 40 |
| 50 | 44 | 40 | 36 | 32 |
| 60 | 37 | 33 | 30 | 27 |
| 75 | 29 | 27 | 24 | 21 |
| 100 | 22 | 20 | 18 | 16 |

INSULIN SENSITIVITY TABLE GRID, POINT DROP PER UNIT OF INSULIN

FIG. 1

METHOD SYSTEM AND DEVICE FOR ASSESSING INSULIN SENSITIVITY

RELATED APPLICATIONS

This application claims priority to and is a continuation of U.S. patent application Ser. No. 12/145,942 filed Jun. 25, 2008, now U.S. Pat. No. 9,244,077, which claims priority to U.S. Provisional Application Ser. No. 60/937,247 filed Jun. 25, 2007, which is herein incorporated by reference in its entirety.

FIELD OF THE INVENTION

Techniques and devices are described relating to sustained medical infusion of therapeutic fluids for patients. In particular, a method, system and device for assessing a diabetic state of the patient is described. For example, the method, system and device can be used for assessing an insulin sensitivity value ("IS"). The assessed IS value can be used, for example, to determine basal and bolus dosages of insulin prior to administrating it to the patient.

BACKGROUND OF THE INVENTION

Diabetes mellitus is a disease of a major global importance. The number of individuals affected increases at almost epidemic rates, such that in 2006, this number reached approximately 170 million people worldwide and is predicted to at least double over the next 10-15 years. Diabetes is characterized by a chronically raised blood glucose concentration (hyperglycemia), due to a relative or absolute lack of the pancreatic hormone-insulin. Within healthy pancreas, beta cells that are located in the islets of Langerhansand continuously produce and secrete insulin according to the blood glucose levels, thereby maintaining near constant levels of glucose in the body. Long-term tissue complication affects both the small blood vessels (microangiopathy, causing eye, kidney and nerve damage) and the large blood vessels (causing accelerated atherosclerosis, with increased rates of coronary heart disease, peripheral vascular disease and stroke). These complications heavily burden the patients and health care resources that are necessary to treat the patients.

The Diabetes Control and Complications Trial (DCCT) demonstrated that development and progression of chronic complications of diabetes are heavily related to the degree of altered glycemia, as quantified by determinations of glycohemoglobin (HbA1 c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia, which may be accomplished by frequently measuring glucose levels and accordingly adjusting an amount of delivered insulin, is of utmost importance.

Conventional insulin pumps can deliver insulin to the patient and can be configured to deliver rapid-acting insulin 24 hours a day through a catheter placed under the skin. The total daily dose (TTD) of insulin can be divided into basal and bolus doses. Basal insulin is delivered continuously over 24 hours and keeps the blood glucose concentration levels (hereinafter, "blood glucose levels") in normal desirable range between meals as well as overnight. Diurnal basal rates can be pre-programmed or manually changed according to various daily activities of the patient. Insulin bolus doses are delivered before meals or during episodes of high blood glucose concentration levels to counteract carbohydrates' loads.

The amount of insulin which should be present in the administered bolus can depend on several parameters, for example:

- Amount of carbohydrates ("Carbs") to be consumed, alternatively defined as "serving", wherein 1 serving equals 15 grams of Carbs.
- Carbohydrate-to-insulin ratio ("CIR"), i.e. an amount of carbohydrate balanced by one unit of insulin which is measured in grams per one unit of insulin.
- Insulin sensitivity ("IS"), i.e. an amount of blood glucose value lowered by one unit of insulin which is measured in mg/dL (milligrams/deciliter) per one unit of insulin.
- Current blood glucose levels ("BSC") which is measured in mg/dL.
- Target blood glucose levels ("TBG"), i.e. a desired blood glucose level. TBG for most patients suffering from diabetes is in the range of 90-130 mg/dL before a meal, and less than 180 mg/dL one to two hours after the start of a meal.
- Residual insulin, i.e. an amount of stored active insulin remaining in the body of the patient after a recent bolus delivery. This parameter is relevant when there is a short time interval between consecutive boluses (i.e. less than 5 hours).

Conventional insulin pumps can require users to constantly calculate or estimate appropriate pre-meal insulin bolus doses. These calculations or estimations can be based on the above mentioned parameters to effectively control the blood glucose levels and maintain euglycemia.

Conventional portable insulin pumps can include bolus calculating means that operate based on inputs of meal carbohydrate content and glucose levels by the patient. In these pumps, the calculated bolus dose can be automatically delivered to the patient.

An example of such conventional pumps is discussed in U.S. Pat. No. 6,936,029 assigned to Medtronic MiniMed. Such a pump provided with a bolus calculator and an algorithm for calculating the amount of insulin to be administered is described. The algorithm is based on a formula for calculating a bolus, depending on the user's IS, CIR, target BG and user inputs of blood glucose (BG) and carbs intake.

If the current BG is higher than the target BG, the recommended bolus is calculated as:

$$\text{Recommended bolus} = \underbrace{(TC/CIR)}_{\text{"Food estimate"}} + \underbrace{(BSC - BST)/IS - RI}_{\text{"Correction estimate"}}$$

Wherein TC—total amount of carbohydrates; CIR—carbohydrate-to-insulin ratio; BST—target blood sugar; BSC—current blood sugar; IS—Insulin sensitivity; RI—remaining insulin, i.e. "insulin on board".

If the current BG is lower than the target BG, the recommended bolus is calculated as:

Recommended bolus=(TC/CIR)+(BSC−BST)/IS

If the current BG is higher than the low target BG and lower than the high target BG (e.g. current blood (BSC) glucose=105 mg/dL, target range (BST)=90-130 mg/dL) then the recommended bolus is calculated as:

Recommended bolus=(TC/CIR)+0

Basal insulin can be delivered continuously over 24 hours, and can keep the blood glucose levels in range between meals and overnight. Diurnal basal rates can be pre-programmed or manually changed according to various daily activities. The basal insulin strongly depend on the user's IS value.

Accurate assessment of the IS value can be critical for maintaining euglycemia for diabetic patients. IS can also be essential in determination of the administered basal dose and the administered bolus dose, especially the correction bolus.

Currently, many type 1 diabetes patients using rapid acting insulin (e.g. Humalog, Novolog) determine their IS value according to the "2200 to 1600 rules". The user's IS is established by dividing the value corresponding to an appropriate rule by the total daily dose of rapid-acting insulin (e.g. if the total daily insulin dose is 40 units and the 1800 rule is used, the insulin sensitivity factor would be 1800 divided by 40=45 mg/dl/unit). FIG. 1 shows the point drop per unit of insulin (insulin sensitivity) according to the various rules (adapted from Using Insulin ©2003)

The derived IS value can be used when initially setting the basal dosages and the bolus calculator of many existing pumps or when the user calculates the necessary bolus. Evaluation of the diabetic progression, especially in type 2 diabetes (insulin sensitivity is inversely related to insulin resistance, the primary etiology of type 2 DM), may be derived from the change in IS value (decreases as the disease progresses).

Using the abovementioned "rules" can have several drawbacks:

- The accurateness of the established IS value is low due to a limited number of applied "rules".
- The values are not re-evaluated throughout the usage of the bolus calculator. This poses a serious problem since the IS value is not a static parameter. This shortcoming may be especially significant for adolescent users due to relatively frequent dynamics of this parameter during puberty.

SUMMARY OF THE INVENTION

A method and a system for determining insulin sensitivity (IS) is described. In one aspect the method and the system can be implemented by receiving a first parameter corresponding to an insulin dose in a subcutaneous tissue; applying a first kinetic model to obtain a plasma insulin concentration based on the first parameter; receiving a second parameter corresponding to a plasma glucose concentration; determining the insulin sensitivity (IS) based on the plasma insulin concentration and the second parameter.

In one implementation, the second parameter can be determined by applying a second kinetic model to a glucose concentration measured in the subcutaneous tissue. For example, the glucose concentration in the subcutaneous tissue can be measured using at least one of a glucometer and a Continuous Glucose Monitor (SCGM).

In one implementation, the insulin sensitivity (IS) can be determined using one or more of conventional plasma glucose-plasma insulin dynamics models. For example, the dynamics models can comprise at least one of the Homeostatic Model Assessment (HOMA), and Quantitative Insulin Sensitivity Check Index (QUICKI).

In one implementation, the insulin sensitivity (IS) can be periodically reevaluated. For example, the insulin sensitivity (IS) can be reevaluated after a predetermined period of time since a last food bolus. In some implementations, the insulin dose in the subcutaneous tissue can be a basal insulin dose.

In some implementations, the method and the system can be implemented by providing a recommendation to a user to validate the determined insulin sensitivity value (IS). For example, the recommendation can be provided as a message displayed on a graphical user interface. In some embodiments, the user can optionally accept or reject the determined insulin sensitivity value (IS). In some embodiments, the determined insulin sensitivity value is accepted automatically.

In some implementations, the method and the system can be implemented by selecting an insulin bolus based on the determined insulin sensitivity value (IS) and delivering the insulin bolus to a user. For example, the insulin bolus can be delivered using a remotely controlled skin securable pump, such that the pump is connectable to and disconnectable from the user's body. In some implementations, the glucose concentration in the subcutaneous tissue can be measured using a glucometer integrated into a remote control unit.

In some implementations, a system that employs a method capable of assessing the user's IS can comprise a miniature skin adhered patch that can continuously dispense insulin and monitor body glucose concentration levels.

In some implementations, a semi closed loop system can be provided. The semi close loop system can monitor glucose levels and dispense insulin according to sensed glucose levels and according to an IS assessment method.

In some implementations, a device that comprises an insulin infusion and a continuous glucose monitor patch unit can also be provided. For example, the monitor patch unit can comprise a disposable part and a reusable part. The reusable part can contain all relatively expensive components and the disposable part can contain cheap components, thus providing a low cost product for the user and a highly profitable product for the manufacturer and payer. The device can employ a method capable of assessing the user's IS value.

In some implementations, an insulin infusion and a continuous glucose monitor patch unit can also be provided. For example, the monitor patch unit can be remotely controlled and can employ a method capable of assessing the user's IS value.

In some implementations, the IS assessment can be established via processing of integrated information obtained from frequent glucose measurements (e.g. subcutaneous continuous glucose monitoring) and data of the delivered basal insulin.

In some implementations, the IS assessment can be obtained from SCII (Subcutaneous Continuous Insulin Infusion), SC glucose sensing and the integration of conventional mathematical models:

- Various mathematical models of the plasma glucose-plasma insulin dynamics exist in the literature. Some of these models have a high predictive capability and were assessed in numerous studies. Insulin sensitivity (IS) can be evaluated by virtue of these models. These models however require the plasma insulin and plasma glucose concentrations—data that may be acquired only by direct blood sampling. In addition, plasma insulin requires a lab analysis (as opposed to blood glucose which can be determined by a portable glucometer).
- There are mathematical models in the literature that exhibit the relationship between plasma glucose and glucose in the interstitial fluid (ISF).
- There are mathematical models in the literature that exhibit the relationship between plasma insulin and insulin in the ISF.

In some implementations, the IS assessment can be obtained from SCII, direct plasma glucose sensing, using a glucometer, and integration of mathematical models exhibiting plasma glucose-plasma insulin dynamics and the relationship between plasma insulin and insulin in the ISF.

In some implementations, the IS can be assessed using one or more of conventional plasma glucose-plasma insulin dynamics models e.g. the "minimal" model is a mathematical model of the plasma glucose-plasma insulin dynamics, proposed by the team of Bergman and Cobelli, the AIDA (www.2aida.org), the model of Sorenson (DIABETES TECHNOLOGY AND THERAPEUTICS, 2005 Vol 7 (1) 94-108). Alternative models which may simplify the insulin sensitivity assessment are for example the Homeostatic Model Assessment (HOMA), and a more recent method is the QUICKI (Quantitative Insulin Sensitivity Check Index). Both employ fasting insulin and glucose levels to calculate insulin sensitivity and both correlate reasonably with the results of the gold standard clamping studies and/or known parameter.

In some implementations, a time delay of 10-20 minutes can be determined between the glucose measured in the ISF and the blood glucose. That is, an ISF glucose measurement made at time "t=20'" is equal to the blood glucose at tome "t".

In some implementations, the IS value can be constantly reevaluated.

In some implementations, the IS value can be reevaluated only in time frames when at least five hours have passed since the last food bolus (e.g. during the night). The IS algorithm in such embodiments only considers the basal insulin.

In some implementations, if a new IS value has been determined, the user can be recommended to pay a visit to his/her practitioner to validate the new IS value, change the settings of the pump accordingly, and possibly perform further tests to evaluate the diabetic state (e.g. HA1C).

In some implementations, if a new IS value is determined, the user may accept the automatically assessed new IS value and change the settings of the device to deliver the following bolus and basal dosages accordingly. In some examples, the automatically assessed new IS value may be set without a user interface.

In some implementations, the user can be notified prior to IS value re-setting and can suspend the re-setting or select an alternative IS value.

In some implementations, the IS value assessment method can be implemented in an insulin infusion device comprising insulin dispensing patch unit and a remote control unit, wherein a glucose sensing apparatus (e.g. glucometer) is integrated in the remote control unit.

In some implementations, the patch unit can be composed of two parts, a reusable part that contains all electronic and driving elements and a disposable part that contains insulin reservoir. The glucose sensing apparatus (e.g. glucometer) may alternatively be integrated in the reusable part of the patch unit of the device. Preferably, the IS value assessment method is implemented in the remote control unit of the insulin infusion device. Alternatively, the IS value assessment method could be implemented in the reusable part of the patch unit of the device. In some implementations that use a glucose sensing apparatus of the device as a glucometer, frequent BG measurements can be performed for the time of the test.

In some implementations, the IS value assessment method can be implemented in the remote control unit of the device. Alternatively, the method can also be implemented in the reusable part of patch unit of the device. Alternatively, the method can be implemented in both the reusable part of the patch unit of the device and the remote control unit of the device.

In some implementations, the IS value assessment method can be implemented by a device configured as a miniature patch that can be adhered to the skin and can continuously dispense insulin and frequently measure glucose levels.

The IS value assessment method can be implemented in a remote unit of an insulin dispensing device that can frequently measure glucose levels. The IS value assessment method can also be implemented in a device comprising a miniature skin adhered patch that can continuously dispense insulin and continuously monitor body glucose concentration levels.

BRIEF DESCRIPTION OF THE DRAWINGS

FIG. 1 shows the point drop per unit of insulin (insulin sensitivity) according to the various rules (adapted from Using Insulin ©2003).

DETAILED DESCRIPTION

Figure 2A:
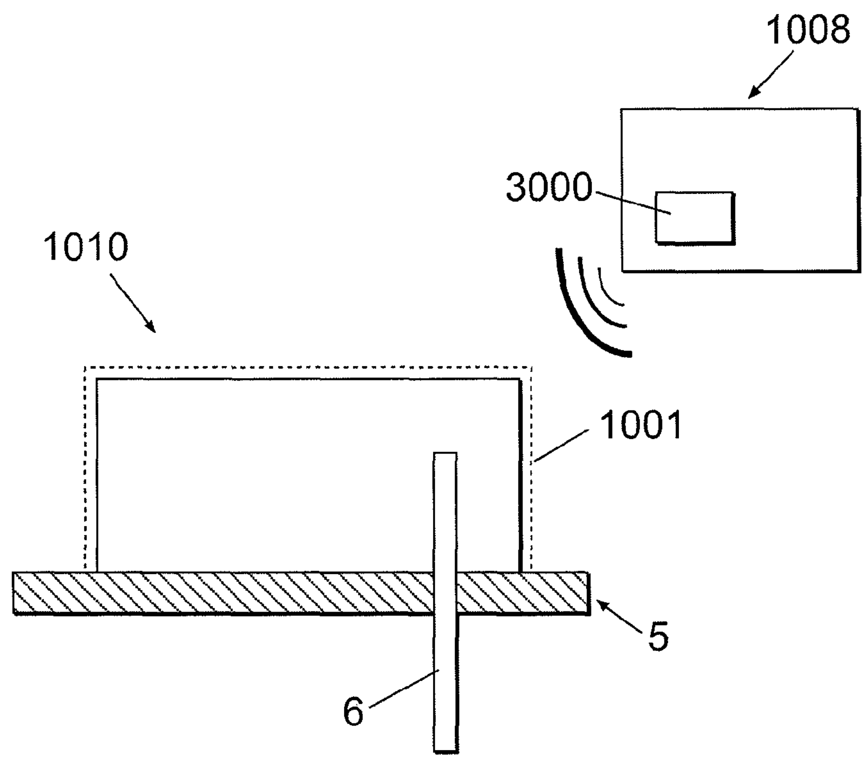
FIGS. 2A-B show an exemplary insulin infusion device comprising an insulin dispensing unit and a remote control unit that contains an IS assessment feature.
Figure 2B:
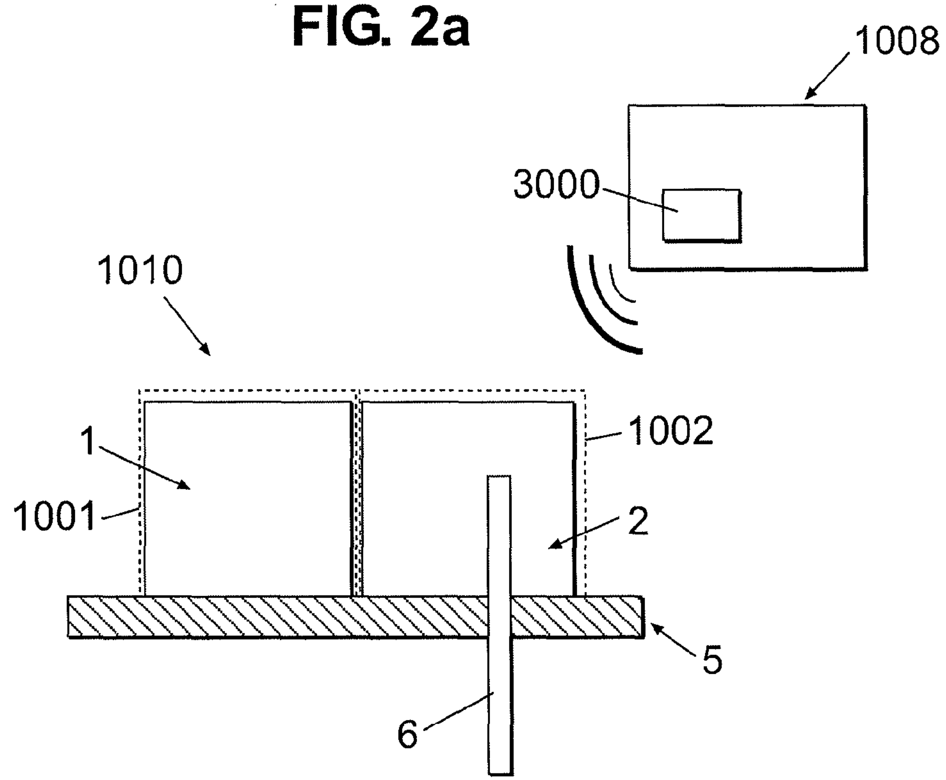

FIGS. 2A-B show an insulin infusion device comprising a patch unit (1010), that can be securable to the patient's skin (5), and a remote control unit (1008), that can communicate with the patch unit (1010), allowing programming, user inputs and data acquisition.

In some implementations, manual inputs can be carried out by buttons (not shown) located on the patch unit (1010). The patch unit (1010) can be composed of one housing (1001) (FIG. 2A) or two housings (1001, 1002) (FIF 2B) containing a reusable part (1) and a disposable part (2) respectively.

The patch unit (1010) can comprise a cannula (6) that can penetrates the skin (5) to allow delivery of insulin. The patch unit (1010) can be directly attached to the patient's skin (5) by adhesive means (not shown) or can be attached to a dedicated needle unit (not shown) that is adhered to the patient skin (5) and allows the patch unit (1010) disconnection from and reconnection to the body as disclosed in our previous patent application U.S. Ser. No. 60/876,679, filed on Dec. 22, 2006. The remote control unit (1008) may contain an insulin sensitivity (IS) assessment feature (3000).

Figure 3A:
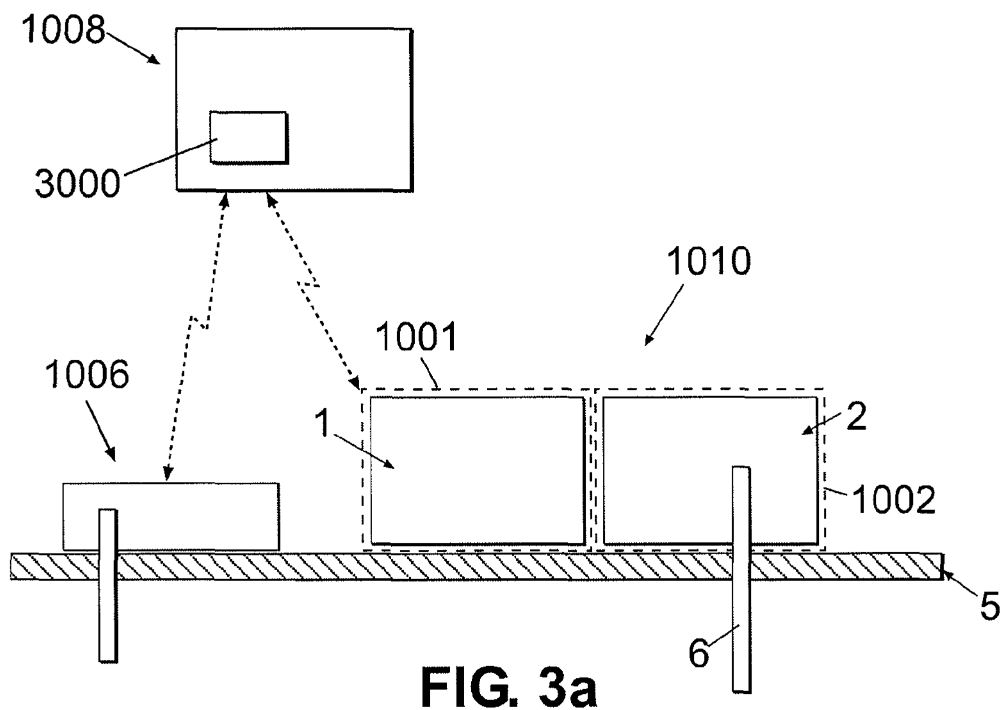
FIGS. 3A-B show an exemplary insulin infusion device containing continuous subcutaneous glucose monitors for providing blood glucose readings (BG) for the IS assessment feature.
Figure 3B:
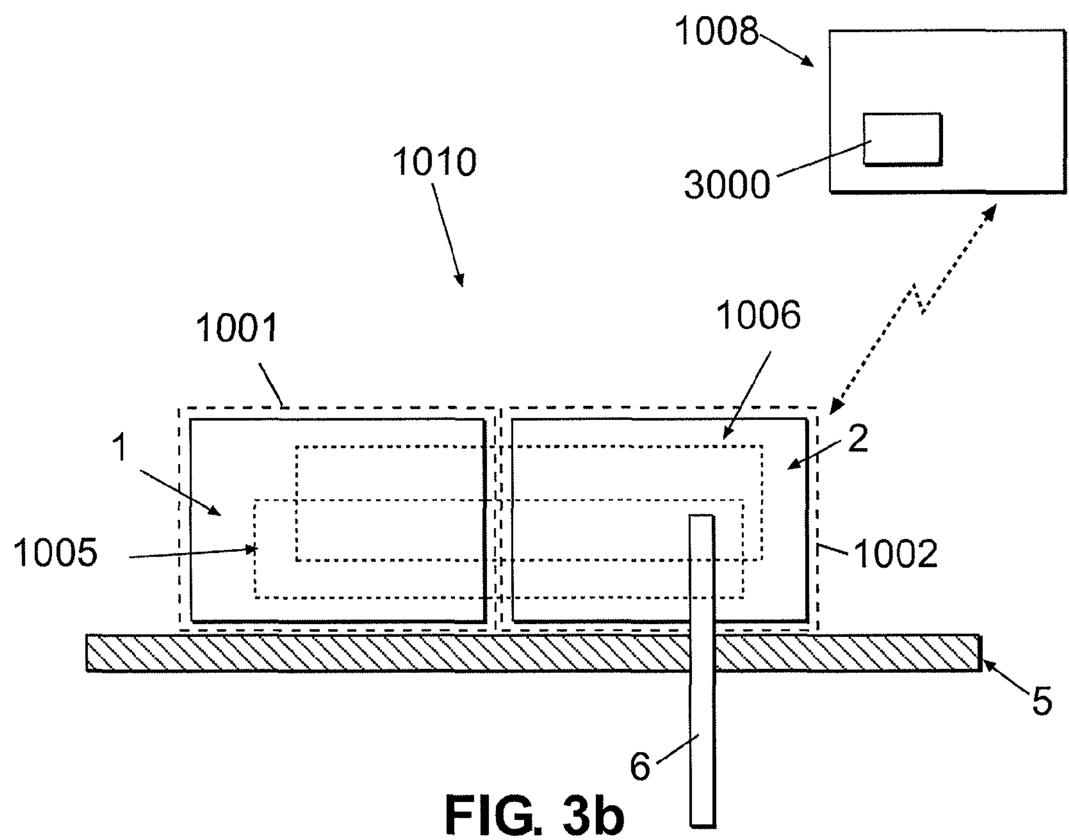

FIGS. 3A-B illustrate several implementations, in which blood glucose level readings needed for the IS assessment feature can be received from a continuous subcutaneous glucose sensing apparatus (1006). The continuous subcutaneous glucose sensing apparatus (1006) and the IS assessment feature (3000) which can be located in the remote control unit (1008) can establish communication therebetween. This communication can allow programming, data handling, and user inputs.

FIG. 3A shows one implementation in which the current blood glucose concentration can be sensed via an independent continuous subcutaneous glucose sensing apparatus (1006). FIG. 3B shows an embodiment in which the continuous subcutaneous glucose sensing apparatus (1006) is located within the patch unit (1010) of the insulin delivery device. The insulin dispensing apparatus (1005) and glucose sensing apparatus (1006) can constitute a single delivery device, and may use a single cannula (6) for both dispensing and sensing. Alternatively (not shown), the dispensing apparatus (1005) and sensing apparatus (1006) can have separate cannulate that penetrate the skin (5) and reside in the subcutaneous tissue.

The delivery device of this embodiment may be composed of two parts—a reusable part (1) and a disposable part (2), each part has a corresponding housing (1001, 1002).

In some implementations, the device can contain a closed loop or semi closed loop system. Insulin can automatically be dispensed according to continuous glucose level monitoring (closed loop) or according to continuous monitoring and additional pre-meal bolus user inputs (semi closed loop). The IS assessment feature (3000) may be used for bolus inputs calculation in the semi closed loop system and for basal dosages administration in the closed and semi-closed loops.

Figure 4:
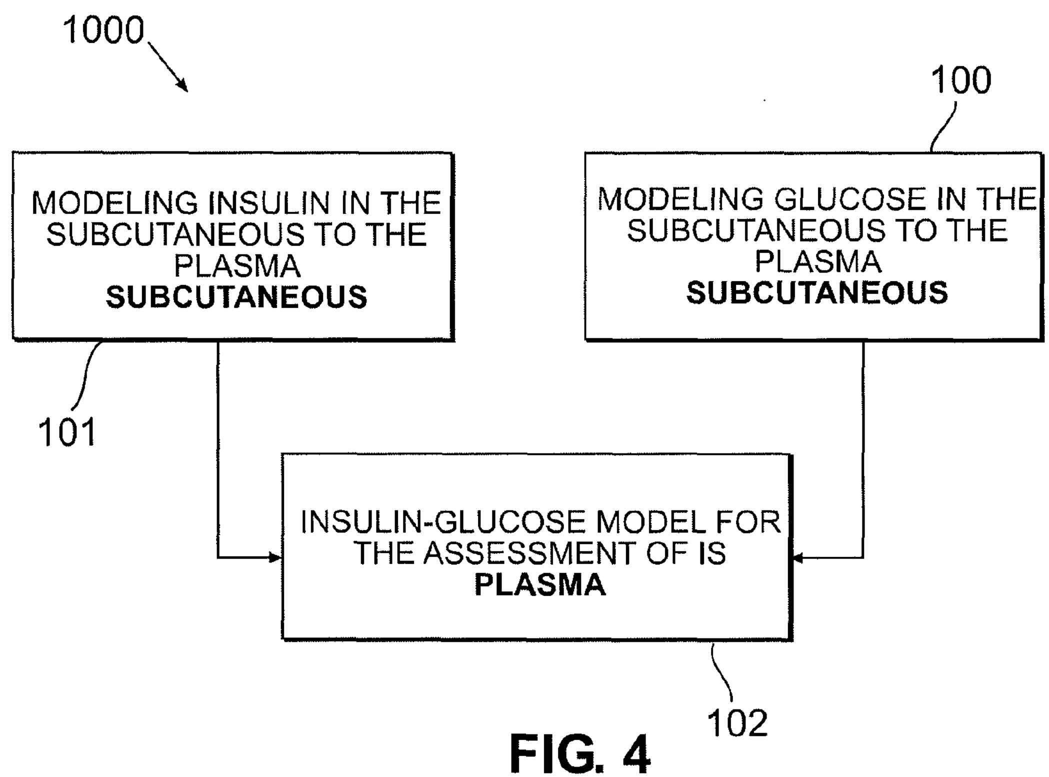
FIG. 4 is a block diagram showing one example of model integration.

FIG. 4 is a schematic block diagram that shows one example of the suggested model, which integrates various sub-modules for the assessment of the IS value. Conventional modeling of the physiological insulin-glucose regulation system can require parameters that must be sampled from the blood tissue (i.e. plasma).

The device disclosed hereinafter, can be attached to the patient's skin and can have accessibility to the subcutaneous tissue layer through the cannula. Thus, sensing of glucose concentration levels in the ISF ("interstitial fluid") can be possible. In addition, the ISF insulin infusion can be carried out and controlled by the patch unit.

The application of "transitional models" (100, 101) can allow the utilization of insulin-glucose conventional models (102) with measured parameters of the subcutaneous tissue (i.e. ISF). It follows that the models (100, 101) can allow transition from the subcutaneous tissue to blood tissue: model (100) simulates the glucose kinetics, and the model (101) simulates the insulin kinetics. This integrated model (1000) can enables IS assessment via parameters which may be acquired thanks to the presence of the adhered patch unit.

Figure 5:
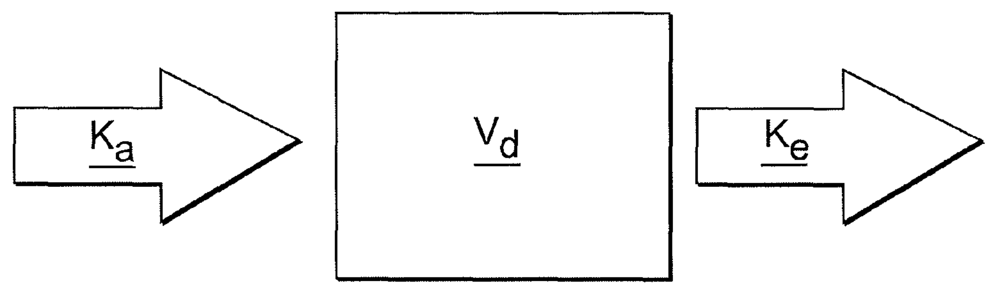
FIG. 5 shows the "Koboyashi" model.

FIG. 5 shows an example of a model (102) that describes the pharmacokinetics of insulin after the administration of continuous infusion in diabetic patients. According to Kobayashy et al., the one-compartment kinetic model can be applied to obtain the plasma insulin from the ISF insulin as schematically shown in FIG. 5. $K_a$ is the first order absorption rate constant and $K_e$ is the first order elimination rate constant. $V_d$ is the distribution volume.

The time course of plasma insulin concentration after continuous subcutaneous infusion at a constant rate (RI) for a given period can be calculated by the following equation:

$$I_0 = \frac{RI}{V_d \cdot K_e} \cdot (1 - e^{K_e \cdot t}) + \frac{RI \cdot (e^{-K_e \cdot t} - e^{-K_a \cdot t})}{V_d \cdot (K_e - K_a)}$$

wherein:

$I_0$ is the plasma insulin concentration at time t during a certain infusion period, RI is a constant rate of insulin infusion to the subcutaneous $K_e$, $K_a$, $V_d$ are pharmacokinetic parameters.

In some implementations, RI is a parameter controlled by the infusion device.

Based on clinical investigation (Kobayashi et al., Diabetes 1983, vol. 32, 331-336), an example for the pharmacokinetic parameters $K_e$, $K_a$, $V_d$ is given below:

$$K_a\ (\text{min}^{-1}) = 0.033 \pm 0.008$$

$$K_e\ (\text{min}^{-1}) = 0.017 \pm 0.002$$

$$V_d\ (\text{L/kg}) = 3.75 \pm 2.28$$

Figure 6:
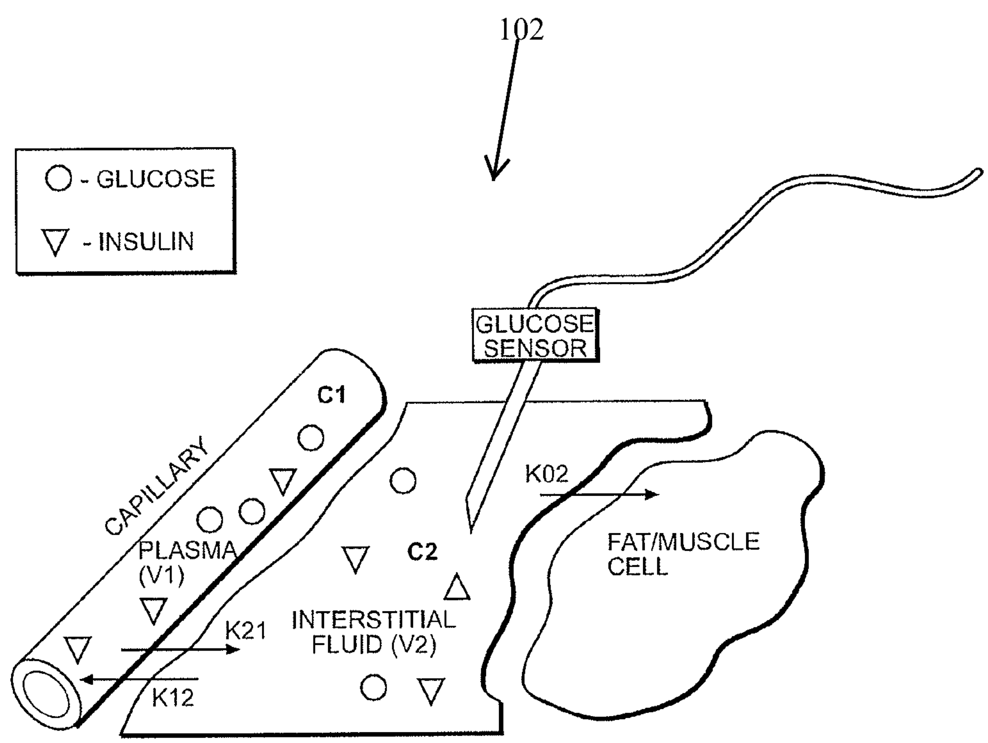
FIG. 6 shows a model of ISF glucose that can predict plasma glucose.

FIG. 6 shows an example of a model (102), proposed by K. Rebrin et al, wherein subcutaneous glucose predicts plasma glucose. The model can describe plasma ($C_1$) and interstitial fluid (ISF; $C_2$) glucose kinetics assuming glucose equilibrates by diffusion ($D = k_{21}V_1 = k_{12}V_2$) and is cleared from ISF by tissue surrounding the sensor (clearance$=k_{02}V_2$), where $V_1$ and $V_2$ represent plasma volume and ISF distribution volume seen by the sensor, respectively. To estimate the gradient and delay the mass balance equation for the ISF pool was first obtained as:

$$\frac{dC_2}{dt} = -(k_{02} + k_{12})C_2 + k_{12}\frac{V_1}{V_2}C_1$$

Where $C_1$ and $C_2$ are plasma and ISF glucose concentrations.

Hence, the ISF-to-plasma glucose gradient and the ISF equilibration time constant (delay) are:

$$C_1 = \frac{k_{12} + k_{02}}{k_{21}\frac{V_1}{V_2}}C_2;\ \tau = \frac{1}{k_{12} + k_{02}}$$

(K. Rebrin et al., Am J Physiol Endocinol Metab 277: 561-571, 1999)

The derivation of plasma glucose may be carried out by such a model in a closed or semi-closed loop system. In alternative embodiments, plasma glucose levels can be detected by a glucometer.

As a simple example, the model (102) for assessing the IS, can be assessed by the quantitative insulin sensitivity check index (QUICKI) suggested by Katz et al. The QUICKI is derived using the inverse of the sum of the logarithms of the fasting insulin and fasting glucose:

$$\frac{1}{\log(I_0) + \log(G_0)}$$

Where $I_0$ is the fasting plasma insulin and $G_0$ is the fasting plasma glucose ($G_0$ is also designated in FIG. 5 as $C_1$). This index correlates well with glucose clamp studies (r=0.78), and is useful for measuring insulin sensitivity (IS), which is the inverse of insulin resistance (IR). In some implementations, these two parameters ($I_0$ and $G_0$) necessary for the model (102) can be obtained from the models (100) and (101) under the condition of fasting.

Figure 7A:
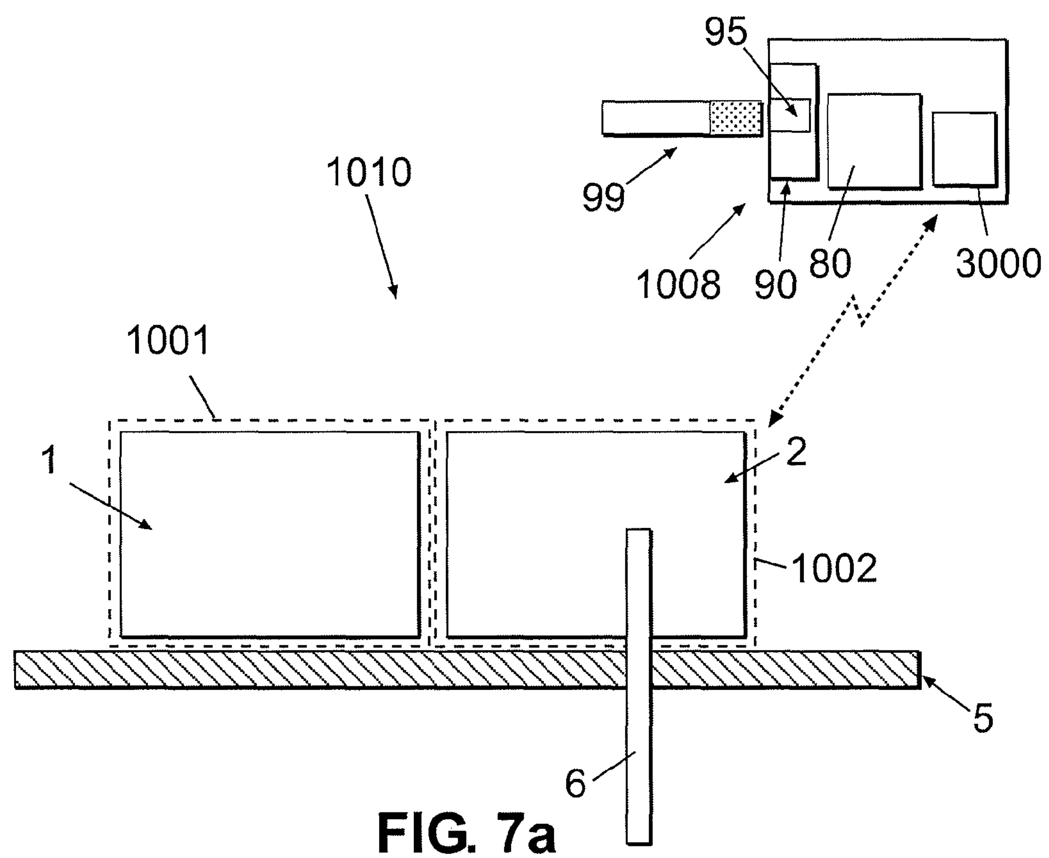
FIGS. 7A-C show exemplary insulin infusion device containing blood glucose monitor in three different locations providing blood glucose (BG) readings for the IS assessment feature.
Figure 7B:
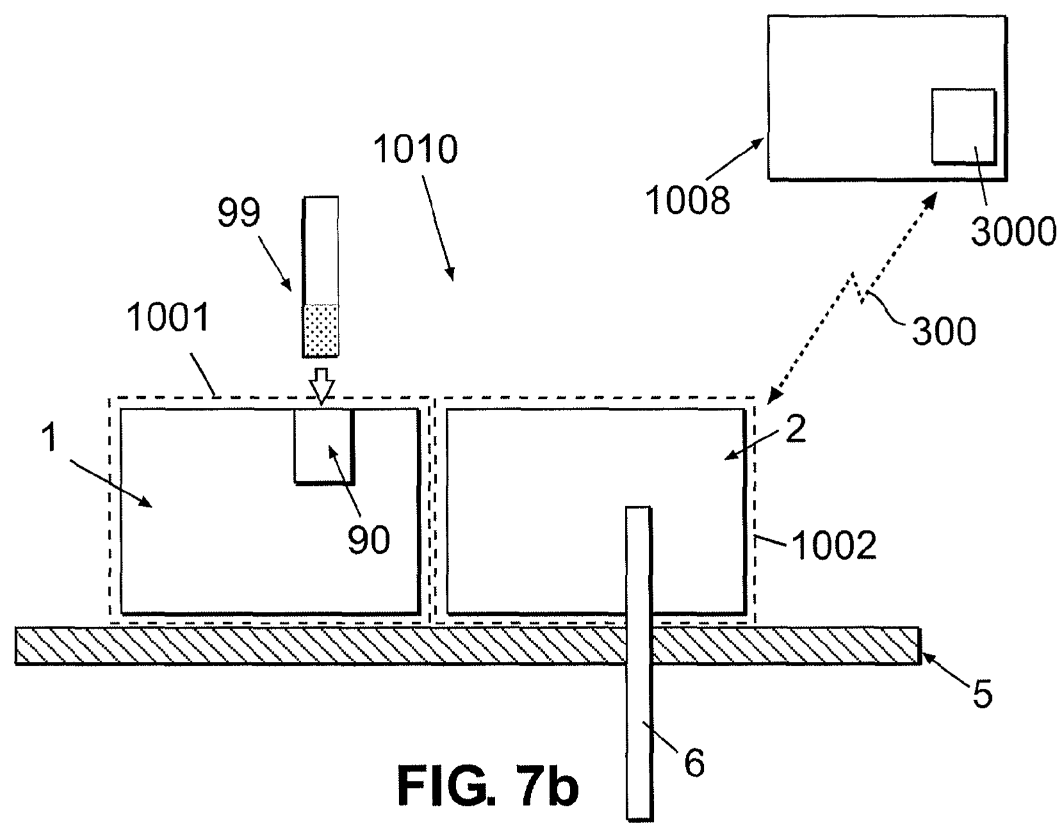
Figure 7C:
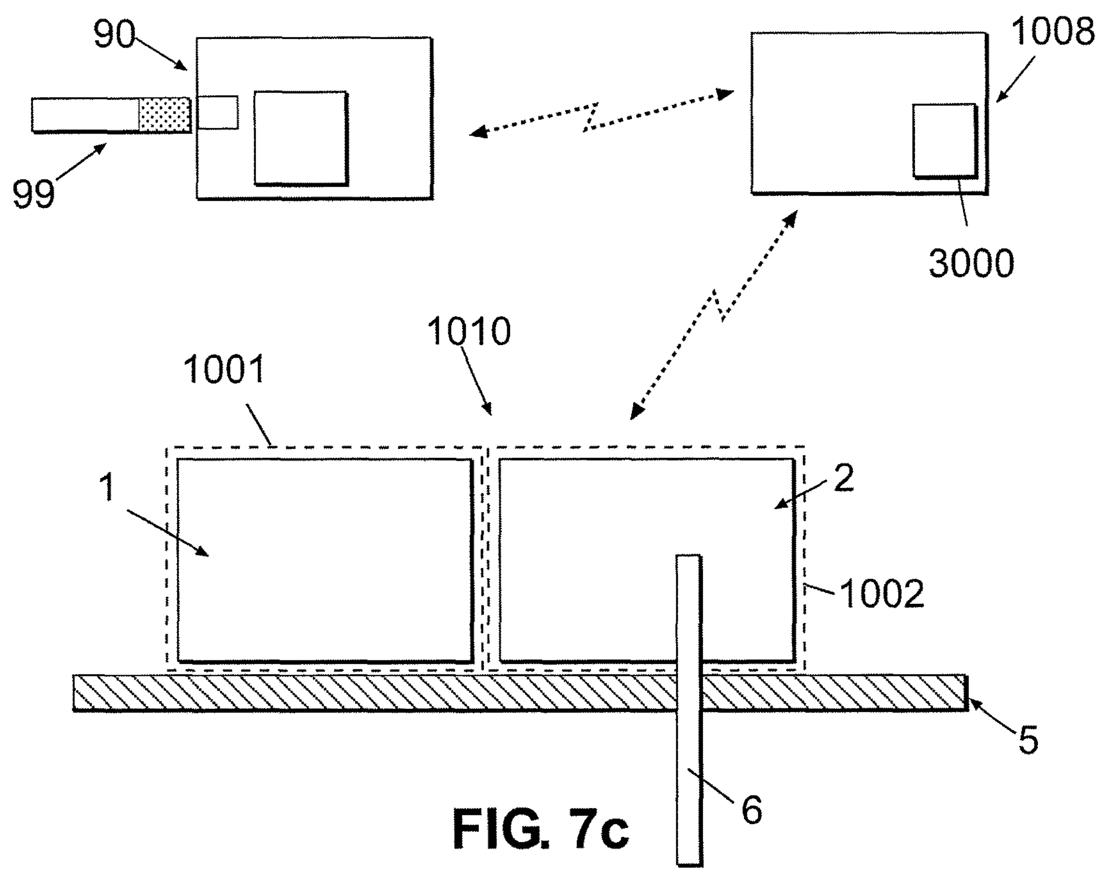

FIGS. 7A-C show three different embodiments of the device, each contains a glucometer (90) to be used as blood glucose (BG) inputs for the IS assessment feature (3000).

FIG. 7A shows a glucometer (90) located in the remote control unit (1008) of the device. The glucometer (90) can comprise an opening (95) for receiving of a test strip (99). The user extracts blood from the body, places the blood on the test strip (99) and inserts the strip into the opening. The glucose readings (90) are displayed on screen (80) of the remote control unit.

FIG. 7B shows a glucometer (90) located in the reusable part (2) of the patch unit (1010). A communication channel (300) between the glucometer (90) residing in the patch unit (1010) and the IS assessment feature (3000) residing in the remote control unit (1008) is maintained, allowing programming, data handling, and user inputs.

FIG. 7C shows an embodiment in which glucose readings are directly or remotely (90) received from an independent glucometer.

Figure 8:
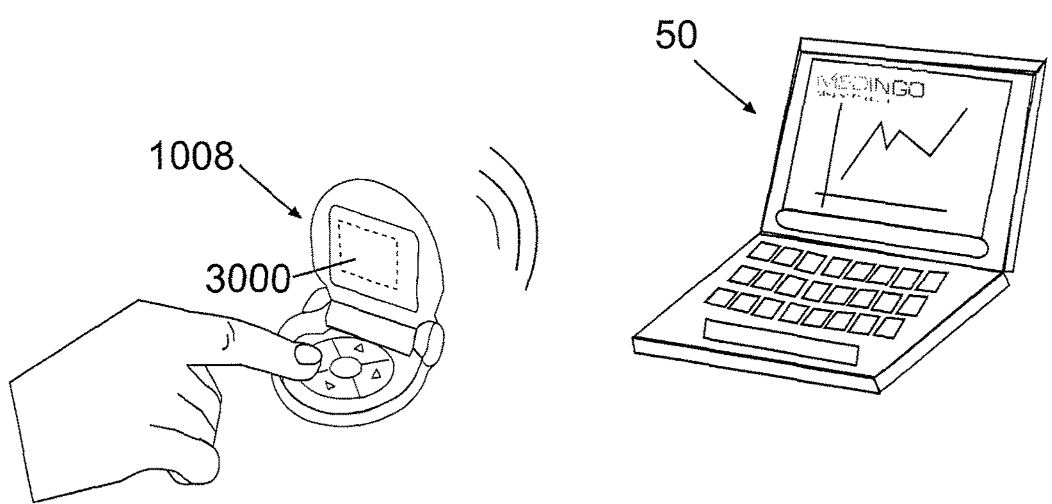
FIG. 8 shows another embodiment of the IS assessment feature assessment feature located in a remote control unit and PC.

FIG. 8 shows another embodiment of the device, where the IS assessment feature (3000) is located in a remote control unit (1008) that communicates with an external PC (50).

In some implementations, any change of the parameters representing the diabetic state of the user (e.g. IS value) can be saved and may be displayed in any graphical or non-graphical manner. The saved data can automatically be sent to the user's practitioner (e.g. by electronic mail) for evaluation, validation or any other clinical intervention.

Any and all patents, applications, articles and/or publications referenced in this specification are hereby incorporated by reference herein in their entireties.

Although illustrative embodiments of the invention have been described in detail herein with reference to the accompanying drawings, it is to be understood that the invention is not limited to those embodiments, and that various changes and modifications can be effected therein by one skilled in the art without departing from the scope and spirit of the invention.

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. These and other embodiments are disclosed or are apparent from and encompassed by, the following description.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways where particular configurations, process steps, and materials disclosed herein as such configurations, process steps, and materials may vary somewhat. In addition, it is to be understood that the phraseology and terminology employed herein are for the purpose of the description and should not be regarded as limiting. Furthermore, as will be apparent to those skilled in the art, the present invention may be embodied in other specific forms without departing from the essential characteristics thereof.

For purposes of the description of the drawings and the embodiments of the present invention, as mentioned for each drawing, each figure may not drawn to scale. Some areas drawn may be bigger and/or simpler in order to clearly portray the improvement to what has already been established. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed. It is also to be understood that the terminology employed herein is used for the purpose of describing particular embodiments only and is not intended to be limiting since the scope of the present invention will be limited only by the appended claims and equivalents thereof.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

The invention claimed is:

1. A method for determining an insulin dose to be administered by an insulin delivery device based on a determined insulin sensitivity (IS), comprising:

receiving, via a subcutaneous glucose sensing apparatus, a first parameter corresponding to a first insulin dose value administered by an insulin dispensing apparatus in a subcutaneous tissue of a patient;

applying a first kinetic model to obtain a plasma insulin concentration based on the first parameter;

sensing a glucose concentration value, via the glucose sensing apparatus, via a cannula that is penetrating and residing in skin of the patient, residing in the subcutaneous tissue;

receiving a second parameter corresponding to the glucose concentration value from the glucose sensing apparatus;

determining the insulin sensitivity (IS) based on the plasma insulin concentration and the second parameter;

determining a second insulin dose value based on the determined insulin sensitivity to be administered by the insulin dispensing apparatus;

reevaluating the insulin sensitivity (IS) after a predetermined period of time since a last food bolus via an insulin sensitivity assessment feature; and delivering an insulin bolus via the cannula coupled to the insulin dispensing apparatus.

2. The method of claim 1 wherein the first kinetic model comprises a one-compartment kinetic model applied to obtain the plasma insulin concentration using a calculation including a first order absorption rate constant, a first order elimination rate constant, and a distribution volume.

3. The method of claim 2 further comprising utilizing in the calculation a time course accounting for continuous subcutaneous insulin infusion at a constant rate.

4. The method of claim 1 further comprising adhering the insulin delivery device directly to the skin of a patient.

5. The method of claim 1 further comprising coupling a glucose sensing device directly to a top inner portion of a housing of the insulin delivery device at a side farthest from a skin surface, such that the glucose sensing device is coupled only to the top inner portion and not inner walls of the housing.

6. The method of claim 1 further comprising providing a glucose sensing device for receiving a test strip, the glucose sensing device being coupled to a housing of the insulin delivery device, the housing having an opening such that the test strip is placeable into the glucose sensing device.

7. A method for determining an insulin dose to be administered by an insulin delivery device based on a determined insulin sensitivity (IS), comprising:

receiving, via an insulin delivery device which comprises a housing containing therein a glucose sensing apparatus and an insulin dispensing apparatus, and having a cannula extending from the housing, a first parameter corresponding to a first insulin dose value administered by the insulin dispensing apparatus in a subcutaneous tissue of a patient;

applying a first kinetic model to obtain a plasma insulin concentration based on the first parameter;

sensing a glucose concentration value, via the glucose sensing apparatus, via the cannula that is penetrating and residing in skin of the patient, residing in the subcutaneous tissue;

receiving a second parameter corresponding to the glucose concentration value from the glucose sensing apparatus;

determining the insulin sensitivity (IS) based on the plasma insulin concentration and the second parameter;

determining a second insulin dose value based on the determined insulin sensitivity to be administered by the insulin dispensing apparatus; and delivering the second insulin bolus value via the cannula.

8. The method of claim 7 further comprising reevaluating the insulin sensitivity (IS) after a predetermined period of time since a last food bolus via an insulin sensitivity assessment feature.

9. The method of claim 7 further comprising coupling a glucose sensing device directly to a top inner portion of the housing farthest from a skin surface, such that it is coupled only to the top inner portion and not inner walls of the housing.

10. The method of claim 7 further comprising providing a glucose sensing device for receiving a test strip, the glucose sensing device being coupled to the housing, the housing having an opening such that the test strip is placeable into the glucose sensing device.

11. The method of claim 10 further comprising placing the test strip into the glucose sensing device via the opening.

12. The method of claim 6 further comprising extracting blood from a body, placing the blood on a test strip, and inserting the test strip into the glucose sensing device via the opening.

13. The method of claim 7 wherein the first kinetic model comprises a one-compartment kinetic model applied to obtain the plasma insulin concentration using a calculation including a first order absorption rate constant, a first order elimination rate constant, and a distribution volume.

14. The method of claim 13 further comprising utilizing in the calculation a time course accounting for continuous subcutaneous insulin infusion at a constant rate.

15. The method of claim 7 further comprising adhering the insulin delivery device directly to the skin of a patient.

* * * * *